US00PP27953P2

(12) United States Plant Patent
Smulders

(10) Patent No.: US PP27,953 P2
(45) Date of Patent: May 2, 2017

(54) APPLE TREE NAMED 'WUR200'

(50) Latin Name: *Malus domestica*
Varietal Denomination: WUR200

(71) Applicant: Rene Smulders, Wageningen (NL)

(72) Inventor: Rene Smulders, Wageningen (NL)

(73) Assignee: Stichting Dienst Landbouwkundig Onderzoek-PPO/PRI, Wageningen (NL)

( * ) Notice: Subject to any disclaimer, the term of this patent is extended or adjusted under 35 U.S.C. 154(b) by 0 days.

(21) Appl. No.: 14/757,068

(22) Filed: Nov. 11, 2015

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — C. A. Whealy

(57) ABSTRACT

A new and distinct cultivar of Apple tree named 'WUR200', characterized by its upright plant habit; moderately vigorous growth habit; numerous fruit produced per plant; fruits with red-colored skin spotted with lenticels; resistance to Apple Scab; and suitability for organic farming practices.

2 Drawing Sheets

Botanical designation: *Malus domestica.*
Cultivar denomination: 'WUR200'.

BACKGROUND OF THE INVENTION

The present invention relates to a new and distinct cultivar of Apple tree, botanically known as *Malus domestica* and hereinafter referred to by the name 'WUR200'.

The new Apple tree is a product of a planned breeding program conducted by the Inventor in Elst, Gelderland, The Netherlands. The objective of the breeding program was to create new Apple trees that produce numerous red-colored fruits that are resistant to Apple Scab (*Venturia inaequalis*), a fungus, which causes severe surface blemishing of the fruit and are suitable for organic farming practices.

The new Apple tree originated from a cross-pollination conducted by the Inventor in Elst, Gelderland, The Netherlands in 1990 of a proprietary selection of *Malus domestica* identified as code number 1971-20153, not patented, as the female, or seed, parent with a proprietary selection of *Malus domestica* identified as code number 1877-10236, not patented, as the male, or pollen, parent. The new Apple tree was discovered and selected by the Inventor as a single plant within the progeny of the stated cross-pollination grown in a controlled environment in Elst, Gelderland, The Netherlands in 2002.

Asexual reproduction of the new Apple tree by vegetative cuttings in a controlled environment in Elst, Gelderland, The Netherlands since 2006 has shown that the unique features of this new Apple tree are stable and reproduced true to type in successive generations.

SUMMARY OF THE INVENTION

The new Apple tree has not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WUR200'. These characteristics in combination distinguish 'WUR200' as a new and distinct Apple tree:

1. Upright plant habit.
2. Moderately vigorous growth habit.
3. Numerous fruit produced per plant.
4. Fruits with red-colored skin spotted with lenticels.
5. Resistant to Apple Scab.
6. Suitable for organic farming practices.

The new Apple tree differs primarily from trees of the female parent selection in fruit production and Apple Scab resistance as trees of the female parent selection produce less fruit per tree than trees of the new Apple tree and trees of the female parent selection are not resistant to Apple Scab. Additionally, trees of the new Apple are more suitable for organic farming practices than trees of the female parent selection.

The new Apple tree differs primarily from trees of the male parent selection in fruit production as trees of the male parent selection produce less fruit per tree than trees of the new Apple tree. Additionally, trees of the new Apple are more suitable for organic farming practices than trees of the male parent selection.

Plants of the new *Malus* can be compared to trees of *Malus domestica* 'Elise', not patented. In side-by-side comparisons conducted in Elst, Gelderland, The Netherlands, the new Apple tree differed primarily from trees of 'Elise' in the following characteristics:

1. Fruits of the new Apple tree were spotted with lenticels whereas fruits of trees of 'Elise' were smooth and not spotted with lenticels.
2. Trees of the new Apple tree were resistant to Apple Scab whereas trees of 'Elise' were not resistant to Apple Scab.

BRIEF DESCRIPTION OF THE PHOTOGRAPHS

The accompanying photographs illustrate the overall appearance of the new Apple tree showing the colors as true as it is reasonably possible to obtain in colored reproductions of this type. Colors in the photographs may differ slightly from the color values cited in the detailed botanical description which accurately describe the colors of the new Apple tree.

The photograph on the first sheet comprises a side perspective view of typical trees of 'WUR200' grown in an outdoor orchard.

The photograph on the second sheet is a close-up view of typical flowering branch of 'WUR200'.

DETAILED BOTANICAL DESCRIPTION

The aforementioned photographs, following observations and measurements describe trees grown during the summer in Randwijk, Gelderland, The Netherlands in an outdoor orchard and under cultural practices typical of commercial Apple tree production. Trees were four years old when the photographs and description were taken. Measurements and numerical values represent averages for typical trees and tree parts. The actual measurements of any individual tree or tree parts, or any group of trees or tree parts, of the new Apple tree may vary from the stated average. In the following description, color references are made to The Royal Horticultural Society Colour Chart, 2001 Edition, except where general terms of ordinary dictionary significance are used.

Botanical classification: *Malus domestica* 'WUR200'.

Parentage:

*Female, or seed, parent*.—Proprietary selection of *Malus domestica* identified as code number 1971-20153, not patented.

*Male, or pollen, parent*.—Proprietary selection of *Malus domestica* identified as code number 1877-10236, not patented.

Propagation:

*Type*.—By vegetative cuttings.

*Time to initiate roots, summer*.—About 8 weeks at temperatures about 24° C.

*Time to initiate roots, winter*.—About 16 weeks at temperatures about 24° C.

*Time to produce a rooted young plant, summer*.—About five months at temperatures about 24° C.

*Time to produce a rooted young plant, winter*.—About eight to ten months at temperatures about 24° C.

*Root description*.—Fibrous, woody; typically brown in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Upright plant habit and moderately vigorous growth habit.

*Tree height*.—About three meters.

*Tree diameter*.—About 80 cm to 150 cm.

*Growth rate*.—About 20 cm to 30 cm per year.

*Trunk description*.—Diameter: About 5 cm to 7 cm. Strength: Strong. Texture: Slightly rough, woody. Color: Close to 200A.

*Lateral branch description*.—Length: About 40 cm to 70 cm. Diameter: About 3 cm to 5 cm. Internode length: About 3 cm to 6 cm. Strength: Strong, firm. Angle of attachment: About 80° from main trunk axis. Texture: Slightly rough, woody. Color: Close to 200A.

*Leaf description*.—Arrangement: Alternate; simple. Length: About 7 cm to 10 cm. Width: About 5 cm to 6 cm. Shape: Ovate to elliptic. Apex: Acute. Base: Cordate, blunt. Margin: Serrate. Texture, upper surface: Smooth, glabrous. Texture, lower surface: Rough, pubescent. Venation pattern: Pinnate. Color: Developing and fully developed leaves, upper surface: Close to 147A; venation, close to 146D. Developing and fully developed leaves, lower surface: Close to 146B; venation, close to 146D. Petioles: Length: About 4 cm to 6 cm. Diameter: About 5 mm. Texture, upper and lower surfaces: Smooth, glabrous. Color, upper and lower surfaces: Close to 146D.

Flower description:

*Flower type and flowering habit*.—Single rotate flowers arranged on panicles; freely flowering habit with about six to ten flowers per inflorescence; flowers face mostly outwardly.

*Fragrance*.—Faintly fragrant, pleasant.

*Natural flowering season*.—Continuously flowering in April and May in The Netherlands.

*Flower longevity*.—Flowers last about two weeks on the plant; flowers not persistent.

*Inflorescence height*.—About 5 cm to 7 cm.

*Inflorescence diameter*.—About 5 cm to 7 cm.

*Flower diameter*.—About 3 cm to 4 cm.

*Flower depth* (*height*).—About 5 mm to 10 mm.

*Flower buds*.—Shape: Oval to rounded. Length: About 1 cm to 2 cm. Diameter: About 1 cm to 1.5 cm. Texture: Smooth, glabrous. Color: Close to N66A.

*Petals*.—Quantity and arrangement: Typically five in a single whorl; slightly imbricate. Length: About 1 cm to 1.5 cm. Width: About 5 mm to 10 mm. Shape: Obovate to elliptic. Apex: Obtuse. Base: Cordate. Margin: Entire; slightly undulate. Texture, upper and lower surfaces: Smooth, glabrous. Luster, upper and lower surfaces: Matte, satiny. Color: When opening, upper surface: Close to 155C tinged with close to 65A mostly towards the apex. When opening, lower surface: Close to 155C flushed with close to N66B. Fully opened, upper surface: Close to 155C tinged with close to 65A mostly towards the apex. Fully opened, lower surface: Close to 155C flushed with close to N66C.

*Sepals*.—Quantity and arrangement: Typically five in a single whorl. Length: About 5 mm to 7 mm. Width: About 3 mm to 5 mm. Shape: Ovate to somewhat deltoid. Apex: Acute to obtuse. Base: Cordate. Margin: Entire. Texture, upper and lower surfaces: Smooth, glabrous. Color, upper and lower surfaces: Close to 146C; towards the apex and base, tinged with close to 187A.

*Pedicels*.—Length: About 3 cm to 5 cm. Diameter: About 2 mm to 4 mm. Strength: Moderately strong. Aspect: About 60° to 90° from stem. Texture: Smooth, glabrous. Color: Close to 147C with spots, close to 187A.

*Reproductive organs*.—Stamens: Quantity: About 20 per flower. Filament length: About 2 cm. Filament color: Close to 155C. Anther length: About 3 mm to 5 mm. Anther shape: Bi-lobed. Anther color: Close to 22A. Pollen amount: Scarce. Pollen color: Close to 158A. Pistils: Quantity: About five per flower. Pistil length: About 1.5 cm. Stigma shape: Trumpet-shaped. Stigma color: Close to 154A. Style length: Less than 1 cm. Style color: Close to 150A. Ovary color: Close to 144A.

Fruit description:

*Ripening time*.—About 160 to 170 days.

*Yield*.—Higher than average.

*Use*.—Fresh market.

*Length*.—About 6 cm to 7 cm.

*Diameter*.—About 7.5 cm to 8 cm.

*Fruit weight*.—Typically individual fruits will weigh between 190 to 230 gr depending on environmental conditions.

*General shape in profile*.—Conical.

*Depth of eye basin*.—Medium, about 8 mm.

*Width of eye basin*.—Medium, about 2 cm.

*Fruit stalk length*.—Medium to long.

*Fruit stalk diameter*.—About 2 mm.

*Fruit stalk color*.—Close to 176A.

*Fruit skin color*.—Ground color, close to 1A, overlain with close to 45A; at harvest, about 75% of the fruit skin is red in color.

*Lenticels*.—Quantity: Numerous, about 10 per square inch. Length: About 2 mm to 3 mm. Color: Close to 153A.

*Flesh texture*.—Firm, compact.

*Flesh color*.—Close to 8D.

*Flavor*.—Rich, aromatic.

*Locules*.—Quantity per fruit: About five. Length: About 1.5 cm. Width: About 5 mm to 10 mm. Shape: Elliptic to ovate.

*Seeds*.—Quantity per locule: None to about three depending on environmental conditions. Length: About 5 mm to 7 mm. Diameter: About 3 mm to 5 mm. Shape: Obovate to elliptic. Color: Close to 200A.

Temperature tolerance: The new Apple tree has been observed to tolerate temperatures ranging from about −20° C. to about 35° C.

Pathogen & pest resistance: Trees of the new Apple have been observed to be resistant to Apple Scab (*Venturia inaequalis*). Trees of the new Apple have not been observed to be resistant to pests and other pathogens common to Apple trees.

It is claimed:

1. A new and distinct Apple tree named 'WUR200' as illustrated and described.

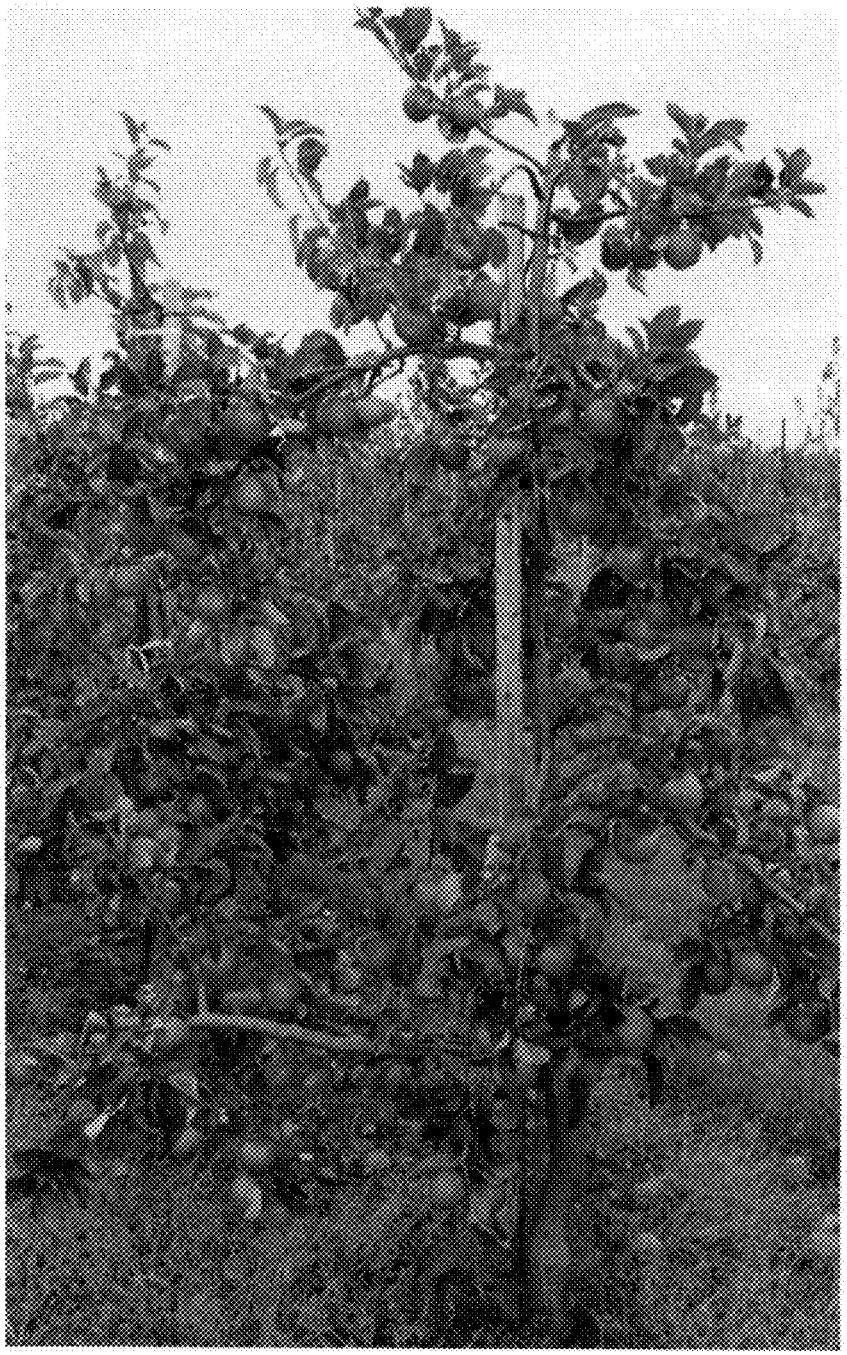

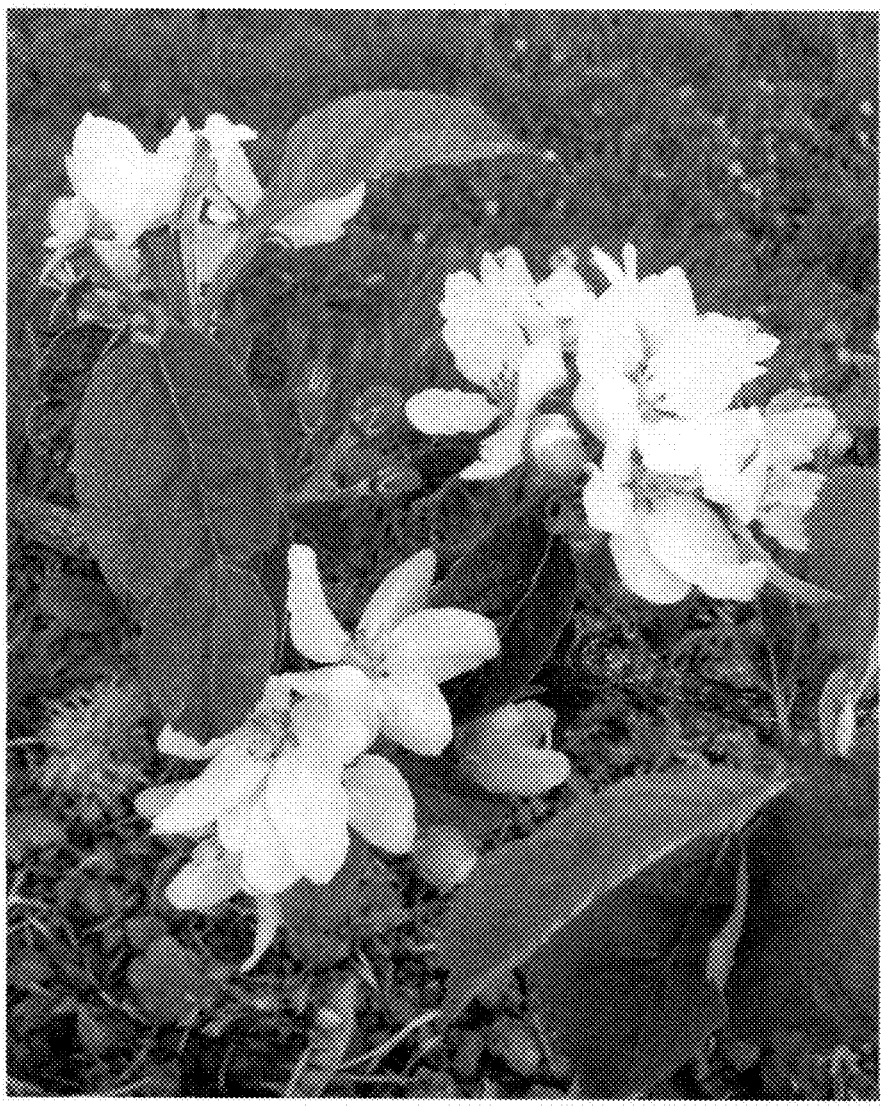

* * * * *